(12) United States Patent
Gomez

(10) Patent No.: US 9,707,125 B2
(45) Date of Patent: Jul. 18, 2017

(54) ICE WRAP

(71) Applicant: Beth Shannon Gomez, Mission Viejo, CA (US)

(72) Inventor: Beth Shannon Gomez, Mission Viejo, CA (US)

( * ) Notice: Subject to any disclaimer, the term of this patent is extended or adjusted under 35 U.S.C. 154(b) by 0 days.

(21) Appl. No.: 13/890,238

(22) Filed: May 8, 2013

(65) Prior Publication Data

US 2016/0296364 A1 Oct. 13, 2016

(51) Int. Cl.
*A61F 7/00* (2006.01)
*A61F 7/02* (2006.01)
*A61F 7/10* (2006.01)

(52) U.S. Cl.
CPC ........ *A61F 7/02* (2013.01); *A61F 2007/0042* (2013.01); *A61F 2007/0231* (2013.01); *A61F 2007/108* (2013.01)

(58) Field of Classification Search
CPC ........ A61F 2007/0042; A61F 2007/004; A61F 2007/0039; A61F 2007/0041; A61F 2007/0043; A61F 2007/0045; A61F 2007/0225; A61F 2007/0231
See application file for complete search history.

(56) References Cited

U.S. PATENT DOCUMENTS

| | | | | |
|---|---|---|---|---|
| 4,805,620 A * | 2/1989 | Meistrell | ............... | A61F 7/08 383/901 |
| 5,133,348 A * | 7/1992 | Mayn | ............... | A61F 7/10 383/901 |
| 5,399,153 A * | 3/1995 | Caprio, Jr. | ............... | A61F 5/0106 602/26 |
| 5,409,500 A * | 4/1995 | Dyrek | ............... | A61F 7/10 607/111 |
| 5,411,541 A * | 5/1995 | Bell | ............... | A61F 7/02 601/15 |
| 5,449,379 A * | 9/1995 | Hadtke | ............... | A61B 17/1325 606/203 |
| 5,470,353 A * | 11/1995 | Jensen | ............... | A61F 7/0097 607/104 |
| 5,728,057 A * | 3/1998 | Ouellette | ............... | A61F 5/0106 602/26 |
| 5,728,147 A * | 3/1998 | Thomas | ............... | A61F 7/00 5/655.9 |
| 5,840,050 A * | 11/1998 | Lerman | ............... | A61F 5/0193 602/19 |
| 5,865,777 A * | 2/1999 | Detty | ............... | A61F 5/0109 602/26 |
| 6,440,159 B1 * | 8/2002 | Edwards | ............... | A61F 7/02 607/108 |
| 6,945,988 B1 * | 9/2005 | Jones | ............... | A61F 7/10 607/108 |

(Continued)

*Primary Examiner* — Kaitlyn Smith
(74) *Attorney, Agent, or Firm* — Loza & Loza, LLP; Michael F. Fedrick

(57) ABSTRACT

A wrap apparatus with 3 equal length radially extending arms with 3 pockets or "sleeves" extending the entire length of the arms to house either ice or heat packs. The radially extending arms wrap around the limb contouring and covering the front, sides, and back of the extremity to supply total ice/heat coverage. The 3 pockets are also wide enough to extend the ice above and below the knee to the adjacent tissues. The ice pack surrounding the extremity, such as a knee or hip, is useful to reduce post-operative swelling.

6 Claims, 5 Drawing Sheets

(56) References Cited

U.S. PATENT DOCUMENTS

| | | | |
|---|---|---|---|
| 7,229,425 B2* | 6/2007 | Dunagan | A61F 13/046 602/14 |
| 7,264,630 B1* | 9/2007 | Webb | A61F 7/02 128/898 |
| D559,393 S * | 1/2008 | Schirrmacher | D24/190 |
| 7,749,182 B2* | 7/2010 | Gramza | A61F 5/0106 602/16 |
| 8,926,539 B2* | 1/2015 | Cropper | A61F 5/0123 602/23 |
| 9,066,788 B2* | 6/2015 | Price | A61F 5/0106 |
| 9,326,911 B2* | 5/2016 | Wyatt | A61H 9/0007 |
| 2001/0034545 A1* | 10/2001 | Elkins | A61F 7/02 607/108 |
| 2002/0052568 A1* | 5/2002 | Houser | A42B 3/00 602/26 |
| 2002/0103520 A1* | 8/2002 | Latham | A61F 7/10 607/108 |
| 2004/0186539 A1* | 9/2004 | Nozik | A61F 13/66 607/108 |
| 2006/0074365 A1* | 4/2006 | Brown | A61F 5/0193 602/24 |
| 2006/0191243 A1* | 8/2006 | Manuel | A01K 13/008 54/79.2 |
| 2007/0161932 A1* | 7/2007 | Pick | A61F 5/0102 602/5 |
| 2007/0167895 A1* | 7/2007 | Gramza | A61F 5/0106 602/26 |
| 2008/0125842 A1* | 5/2008 | Petitt | A41D 13/0012 607/108 |
| 2008/0188786 A1* | 8/2008 | Hickling | A61F 5/0104 602/26 |
| 2008/0195012 A1* | 8/2008 | Miros | A61F 5/0106 602/26 |
| 2008/0245361 A1* | 10/2008 | Brown | A61H 9/0078 128/118.1 |
| 2008/0249440 A1* | 10/2008 | Avitable | A61H 9/0078 601/151 |
| 2008/0249441 A1* | 10/2008 | Avitable | A61H 9/0078 601/151 |
| 2008/0249442 A1* | 10/2008 | Brown | A61H 9/0078 601/152 |
| 2008/0249443 A1* | 10/2008 | Avitable | A61H 9/0078 601/152 |
| 2008/0249444 A1* | 10/2008 | Avitable | A61H 9/0078 601/152 |
| 2008/0249449 A1* | 10/2008 | Brown | A61F 13/085 602/20 |
| 2008/0249455 A1* | 10/2008 | Brown | A61H 9/0078 602/75 |
| 2009/0020521 A1* | 1/2009 | Blaszczykiewicz | A61F 7/007 219/529 |
| 2009/0112134 A1* | 4/2009 | Avni | A61H 23/0263 601/15 |
| 2009/0247925 A1* | 10/2009 | Purcell | A61F 7/06 602/75 |
| 2009/0312681 A1* | 12/2009 | McSpadden | A61F 5/0123 602/2 |
| 2010/0152823 A1* | 6/2010 | Muchowicz | A61F 7/10 607/112 |
| 2010/0292622 A1* | 11/2010 | Weissleder | A61F 5/0193 602/23 |
| 2010/0312316 A1* | 12/2010 | Kim | A45D 29/00 607/108 |
| 2010/0324626 A1* | 12/2010 | Lefkovitz | A61N 1/0484 607/51 |
| 2011/0004133 A1* | 1/2011 | Viner | A61F 7/10 602/14 |
| 2011/0009931 A1* | 1/2011 | Hong | A61F 7/10 607/112 |
| 2011/0066218 A1* | 3/2011 | Geibel | A61F 7/02 607/112 |
| 2013/0060178 A1* | 3/2013 | Vollbrecht | A61F 5/0109 602/5 |
| 2014/0052035 A1* | 2/2014 | Britt | A61F 5/012 602/2 |
| 2014/0081187 A1* | 3/2014 | Wyatt | A61H 7/007 601/152 |
| 2015/0327969 A1* | 11/2015 | Entler | A61F 7/08 602/79 |

* cited by examiner

ICE WRAP

BACKGROUND

After surgery or an injury, physicians and physical therapists recommend icing affected sites at least 4 times a day. Ice machines are immobile and high maintenance, often requiring a caregiver to fill up the ice machine with new ice every 3 hours. Ice bags are messy and do not stay in place.

U.S. Pat. No. 5,133,348 by Mayn discloses an ice pack that contours around a body part and has extending arms. This ice pack, however, is not big enough to complete surround the lower thigh and upper calf, where post-operative swelling is often located.

U.S. Pat. No. 5,728,057 by Ouellette discloses an elastic knee wrap with 3 straps extending in the same direction to wrap around the knee. It has an opening over the patella and allows for knee flexion and extension. This knee wrap does not provide pockets inside the straps, nor does it provide space for an ice pack to reduce swelling.

U.S. Patent Publication No. 2008-012584 by Petitt is a compression garment that also has pockets to house ice packs. The pockets are located around muscular areas, but do not surround the knee or hip joints.

SUMMARY

One of the consequences of knee surgery is pain and swelling. The more swelling, inflammation, pain, and tightness a patient experiences after surgery, the more difficulty a patient has with bending and straightening his or her knee. Excessive pain and swelling ultimately delays recovery. Icing regularly has been proven to reduce swelling and reduce tightness (usually described as a "tight rubber band around the knee"), resulting in improved tolerance for range-of-motion and therefore reducing recovery time.

The present ice wrap has a unique design to optimize ice coverage around the front, sides, and back of the knee. It is designed for post-operative patients recovering from knee surgery. Prior ice packs do not wrap completely around the knee, lower thigh and upper calf to address the entire swollen joint and neighboring tissues. The few ice packs that do wrap around the knee are usually rectangular in shape, non-contouring, uncomfortable, heavy, or too small to address swelling in the adjacent tissues.

The present ice wrap comprises 3 radially extending arms that project and attach in a "tongue and groove" fashion to provide a contouring feature anteriorly to posteriorly ("A-P"), wherein one arm extending anteriorly fits between a pair of arms extending posteriorly, when wrapped around a subject's limb, for example. "A-P" stands for anterior to posterior (front to back) and is designed for total knee replacement or total hip replacement patients who develop swelling throughout the joint after surgery.

The ice wrap is long enough to cover associated adjacently inflamed tissues above and below the affected joint which are often affected after knee and hip surgery, and is made from a material that contains woven and flexible properties to provide compression to the extremity to assist with swelling and edema reduction. The present ice wrap can be used for example to reduce swelling for total knee replacement patients, total hip replacement patients, arthroscopic knee or hip patients, knee ligament repairs (ACL, for example), hip labral repairs, non-surgical injuries to the knee and hip, and femoral, tibia/fibula, or pelvic fractures.

The present invention also includes a method for treating pain, inflammation and swelling associated with post-operative knee or hip surgery by placing the present ice wrap with ice packs inside the sleeves on an affected area and pulling the ice wrap snugly around the extremity for total ice coverage.

FIGURES

FIG. 1. is a top plan view of the ice pack of the current invention.

FIG. 2. shows the opening of the pocket to the sleeve that holds the ice pack or heat pack the length of the sleeve.

FIG. 3. is a bottom plan view of the ice pack of the current invention.

FIG. 4. illustrates the use of the present invention on a knee, upper calf, and lower thigh of a subject.

FIG. 5. illustrates the use of the present invention on a hip, SI joint, and upper thigh of a subject.

DESCRIPTION

The present tongue and groove ice wrap contours around the joint and adjacent tissues, provides total anterior to posterior coverage, provides a sleeve to insert an ice pack, and applies compression around the extremity. However, this product is not limited to total knee or total hip replacement patients. Patients recovering from arthroscopy, ligament repairs (ACL for example), labral repairs, fractures, or non-surgical candidates also benefit from this ice wrap design.

Figure 1:
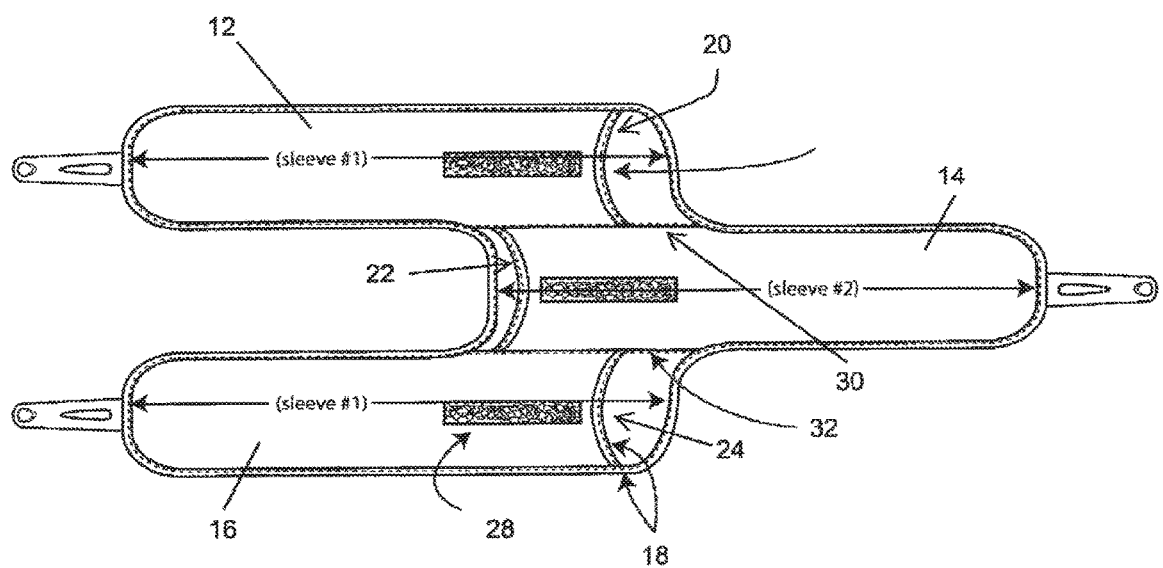
FIG. 1 shows a top plan view of the current invention with 3 extending arms, 12, 14, and 16 with stitching, 30, 32 through the upper and lower layers to create their own sleeves, 20, 22, 24 to contain an ice pack or heat pack.
Figure 2:
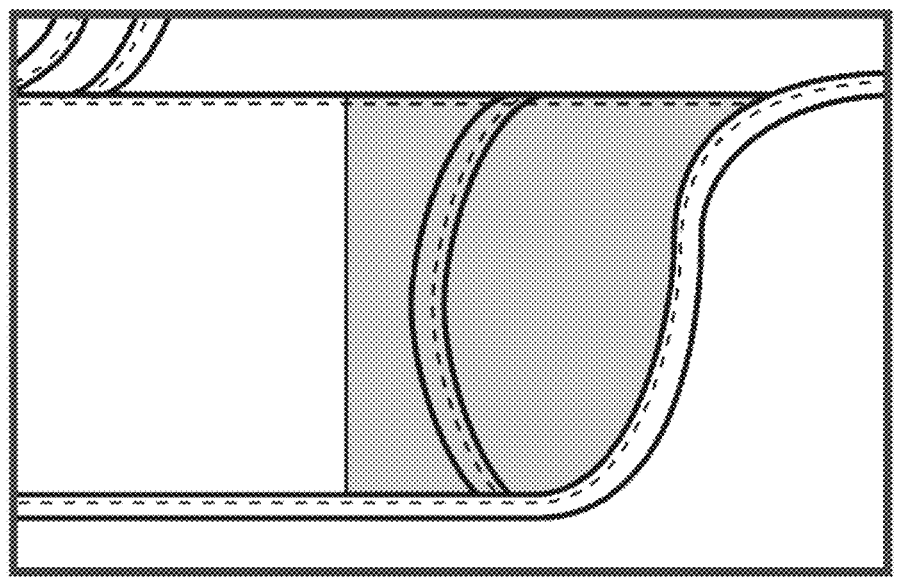
FIG. 2 shows corner piece under the top layer, creating a simple envelope style opening for the sleeves, 20, 22, and 24 shown in FIG. 1.
Figure 3:
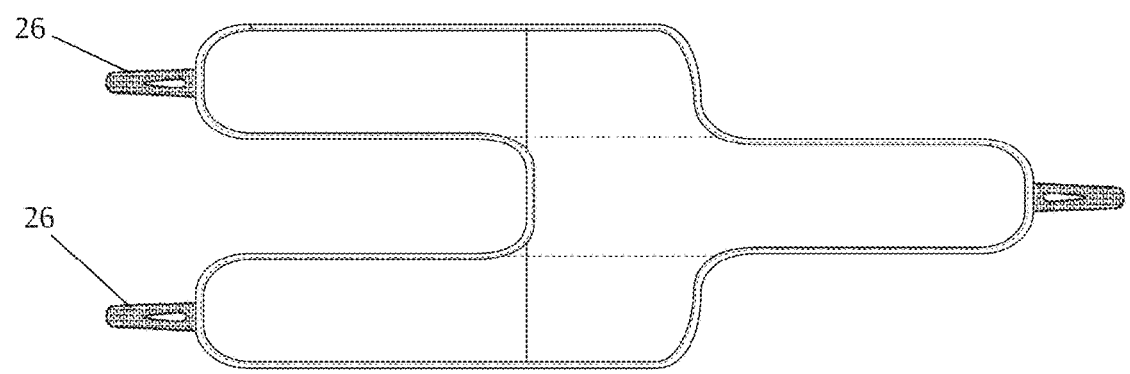
FIG. 3 shows the bottom view of the ice pack with Velcro hooks, 26, at the distal ends of the 3 radially extending arms which can wrap around and attach to the Velcro loops, 28, located on the proximal end of the 3 arms shown in FIG. 1.
Figure 4:
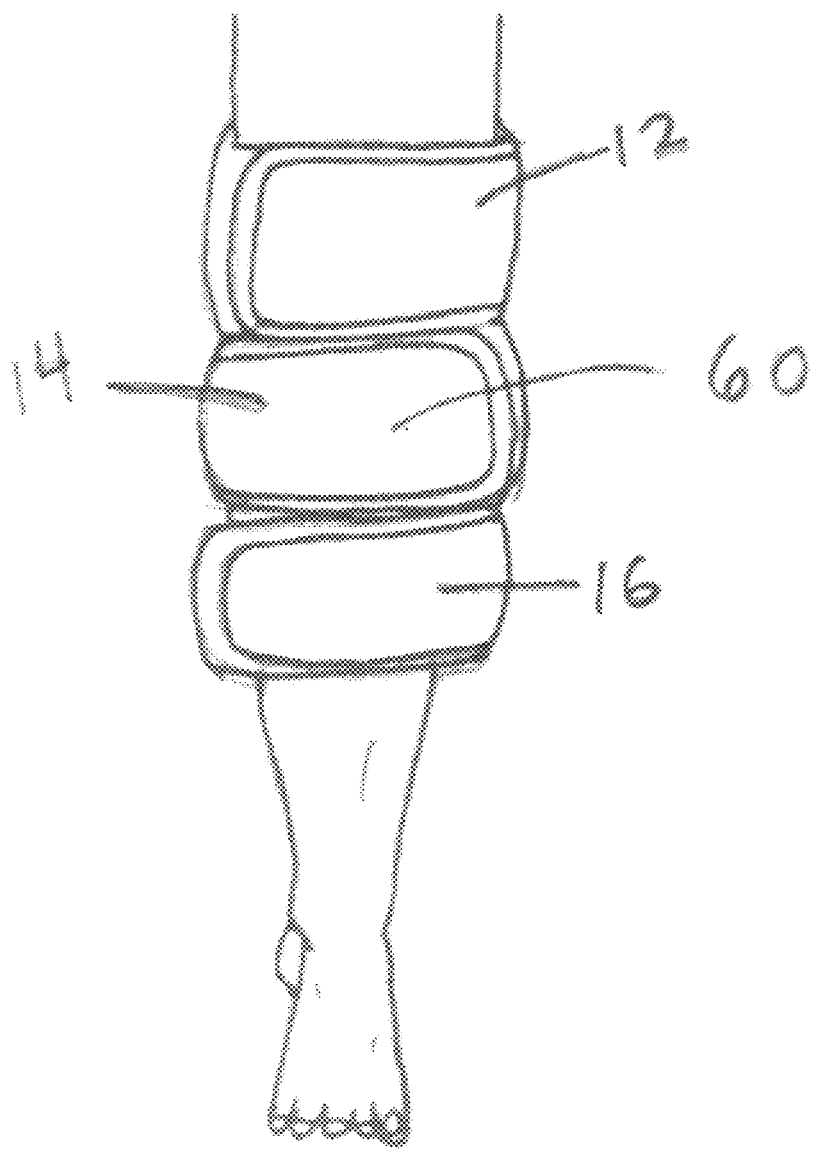

FIG. 4 shows the ice wrap on a patient's knee, 60. The ice wrap totally surrounds the front, sides, and back of the knee, lower thigh, and upper calf to decrease post-operative swelling, pain, and edema. The middle of the ice wrap is centered over the patella. The upper, 12, middle, 14, and lower, 16, radially extending arms are pulled snugly around the sides and posterior aspect of the knee, thigh, and calf and attached by the Velcro, 26 to 28. The ice pack contours around the entire knee, lower thigh and upper calf giving total ice coverage.

Figure 5:
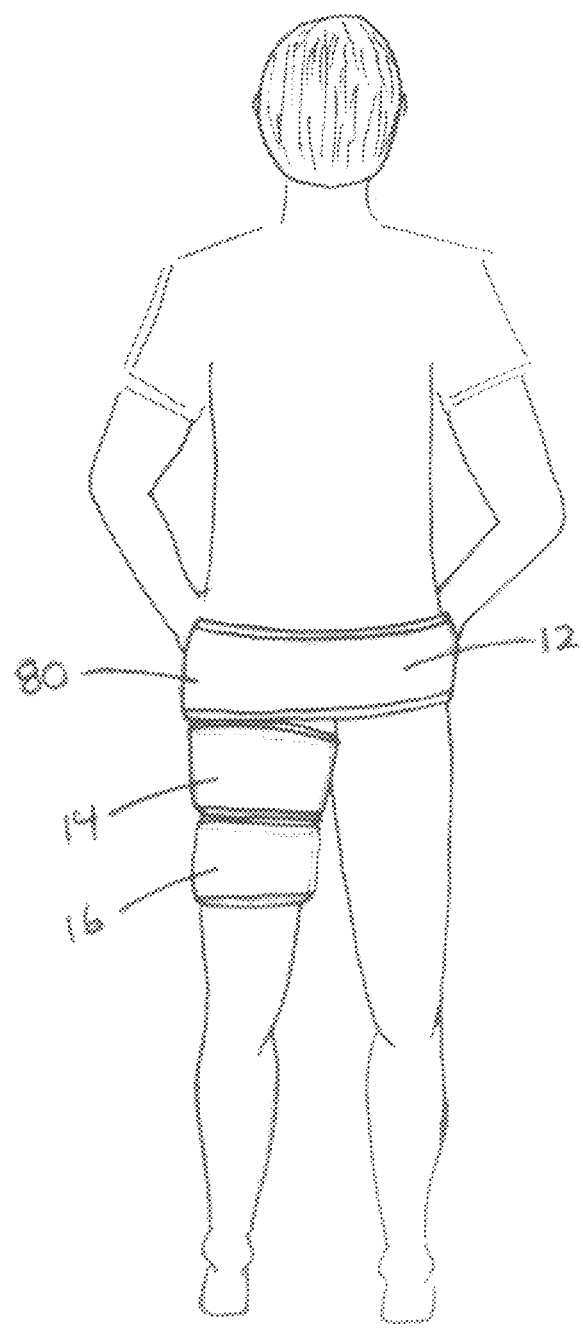

FIG. 5 shows the ice wrap on a patient's hip, 80. The ice wrap totally surrounds the front, sides, and back of the hip, and upper thigh to mid-thigh to decrease post-operative swelling, pain, and edema. The middle of the ice wrap is centered over the lateral hip. The upper 12, middle 14, and lower 16, radially extended arms are pulled snugly around the hip and thigh and attached by the Velcro. The ice pack contours around the entire hip and thigh giving total ice coverage.

Features

1. A mobile wrap apparatus for applying cryo-therapy (or heat therapy) to the front, sides, and to the back of the knee concurrently.

2. The wrap apparatus has a middle area that is applied over the patella; with 3 extending arms, that are a certain length, run transverse to the thigh and leg, and are long enough to make a wrap around the knee, thigh, and leg.
3. The upper and lower arms radially extend transversely to the limb.
4. The middle arm radially extends transversely to the limb, in the opposite direction of the top and bottom arms.
5. The upper and lower arms run parallel to each other with a concave opening with space between the upper and lower arms. The middle arm, is convex, and when wrapped around the knee, fits into the concave space between the upper and lower arms, like a "tongue and groove" attachment.
6. Each arm has a distal Velcro hook portion that wraps around the extremity and attaches to the central Velcro loop portion.
7. The arms each contain an opening pocket, sleeve, that houses a cold pack (or heat pack) that extends the entire length of the sleeve to provide a cooling (or heating) effect to the front, sides, and back of the knee.
8. The material that approximates the skin is made of flexible and woven properties that provide compression to the extremity.
9. The wrap apparatus is a flexible shape and when applied to the extremity contours around the extremity to provide total anterior to posterior ice (or heat) coverage.

METHOD OF USE

STEP 1: Place ice insert in a freezer overnight.
STEP 2: Once frozen, slide the ice inserts into each sleeve of the Ice Wrap. There are 3 sleeves and 3 ice packs. The ice packs should slide to the end of the sleeve for optimal ice coverage.
STEP 3: Straighten leg and center Ice Wrap over the knee cap.
STEP 4: Pull the middle arm snugly behind the back of the knee and fasten to the middle Velcro.
STEP 5: Pull the upper arm snugly behind the back of the thigh and fasten to the top Velcro.
STEP 6: Pull the lower arm snugly behind the back of the thigh and fasten to the bottom Velcro.
STEP 7: Elevate lower extremity above the heart with 2-3 pillows.
STEP 8: Remove Ice Wrap after 20-30 minutes of application.
STEP 9: Fold Ice Wrap as directed and place into freezer for approximately 2 hours between applications.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure.

Recitation of value ranges herein is merely intended to serve as a shorthand method for referring individually to each separate value falling within the range. Unless otherwise indicated herein, each individual value is incorporated into the specification as if it were individually recited herein. All references cited herein are incorporated by reference in their entirety.

What is claimed is:

1. A knee wrap having a proximal end, a distal end, and a medial portion, the knee wrap comprising:
    a first arm having a proximal end, a distal end, and two longitudinal sides extending between the proximal end and the distal end of the first arm, wherein the first arm comprises a first sleeve for retaining an ice pack, the first sleeve extending along the length of the first arm, wherein the first sleeve has a closed end at the proximal end of the first arm and an open end at the distal end of the first arm;
    a second arm having a proximal end, a distal end, and two longitudinal sides extending between the proximal end and the distal end of the second arm, wherein the second arm comprises a second sleeve for retaining an ice pack, the second sleeve extending along the length of the second arm, wherein the second sleeve has a closed end at the distal end of the second arm and an open end at the proximal end of the second arm; and
    a third arm having a proximal end, a distal end, and two longitudinal sides extending between the proximal end and the distal end of the third arm, wherein the third arm comprises a third sleeve for retaining an ice pack, the third sleeve extending along the length of the third arm, wherein the third sleeve has a closed end at the proximal end of the third arm and an open end at the distal end of the third arm,
    wherein a first longitudinal side of the second arm is attached at the proximal end to a longitudinal side of the first arm at the distal end of the first arm, and wherein a second longitudinal side of the second arm is attached at the proximal end to a longitudinal side of the third arm at the distal end of the third arm, so that the first arm, the second arm, and the third arm are connected in the medial portion of the knee wrap,
    wherein each of the sleeves comprises an upper layer of flexible material and a lower layer of flexible material, each sleeve being formed by stitching the upper layer of flexible material to the lower layer of flexible material, the stitching extending around the periphery of each sleeve, and
    wherein the first arm and the third arm extend from the medial portion in a first direction and the second arm extends from the medial portion in a second direction opposite the first direction such that the second arm fits between the first arm and the third arm when the knee wrap is wrapped around a subject's leg or hip.

2. The knee wrap of claim 1, further comprising an ice pack configured to fit within any of the sleeves of the knee wrap.

3. The knee wrap of claim 2, wherein the ice pack comprises a liquid material.

4. The knee wrap of claim 2, wherein the ice pack comprises a gel.

5. The knee wrap of claim 1, wherein each arm comprises a hook and loop fastener, the hook portion of the hook and loop fastener being on one longitudinal end of the arm and the loop portion of the hook and loop fastener being on the other longitudinal end of the arm.

6. A method for treating a subject with pain, inflammation or swelling associated with post-operative knee or hip surgery, comprising the steps of:
    providing the knee wrap of claim 1;

placing ice packs in the sleeves of each of the arms of the knee wrap; and wrapping the first arm, the second arm, and the third arm around a leg and/or hip of the subject.

* * * * *